(12) United States Patent
Zhao et al.

(10) Patent No.: US 9,301,676 B2
(45) Date of Patent: Apr. 5, 2016

(54) SYSTEM AND METHOD FOR DETERMINING OCULAR SCATTERING

(71) Applicant: Abbott Medical Optics Inc., Santa Ana, CA (US)

(72) Inventors: Huawei Zhao, Irvine, CA (US); Li Chen, San Jose, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 52 days.

(21) Appl. No.: 14/452,856

(22) Filed: Aug. 6, 2014

(65) Prior Publication Data

US 2015/0042955 A1 Feb. 12, 2015

Related U.S. Application Data

(60) Provisional application No. 61/862,695, filed on Aug. 6, 2013.

(51) Int. Cl.
*A61B 3/10* (2006.01)
*A61B 3/00* (2006.01)

(52) U.S. Cl.
CPC ............. *A61B 3/10* (2013.01); *A61B 3/0008* (2013.01)

(58) Field of Classification Search
USPC .................................................. 351/221, 246
See application file for complete search history.

(56) References Cited

U.S. PATENT DOCUMENTS

| | | | |
|---|---|---|---|
| 4,665,913 | A | 5/1987 | L'Esperance, Jr. |
| 4,669,466 | A | 6/1987 | L'Esperance |
| 4,732,148 | A | 3/1988 | L'Esperance, Jr. |
| 4,764,930 | A | 8/1988 | Bille et al. |
| 4,770,172 | A | 9/1988 | L'Esperance, Jr. |
| 4,773,414 | A | 9/1988 | L'Esperance, Jr. |
| 4,863,261 | A | 9/1989 | Flammer |
| 5,108,388 | A | 4/1992 | Trokel et al. |
| 5,163,934 | A | 11/1992 | Munnerlyn |
| 5,207,668 | A | 5/1993 | L'Esperance, Jr. |
| 5,219,343 | A | 6/1993 | L'Esperance, Jr. |
| 5,646,791 | A | 7/1997 | Glockler |
| 5,993,438 | A | 11/1999 | Juhasz et al. |
| 7,931,371 | B2 | 4/2011 | Dai |
| 2004/0183997 | A1 | 9/2004 | Suzuki |

OTHER PUBLICATIONS

International Search Report and Written Opinion for Application No. PCT/US2014/049886 mailed on Oct. 24, 2014, 7 pages.

*Primary Examiner* — Jack Dinh
(74) *Attorney, Agent, or Firm* — Abbott Medical Optics Inc.

(57) ABSTRACT

Improved systems and methods for determining ocular scattering are provided. These systems and methods can be used to quantify ocular scattering before and/or after a wide variety of different ophthalmic diagnostic procedures, and various surgical and non-surgical treatments. One embodiment provides a system and method for determining ocular scattering that uses two light detectors, with one detector configured to detect light over a relatively narrow angular range, and the other detector configured to detect light over a relatively large angular range. The data from the narrow angular range and the large angular range can then be analyzed to determine a measurement of ocular scattering.

32 Claims, 6 Drawing Sheets

SYSTEM AND METHOD FOR DETERMINING OCULAR SCATTERING

CROSS-REFERENCES TO RELATED APPLICATIONS

This application claims priority to U.S. provisional application No. 61/862,695 filed on Aug. 6, 2013, the entire contents of which are incorporated herein by reference.

TECHNICAL FIELD

This invention relates to vision techniques and particularly to techniques for determining ocular scattering.

BACKGROUND OF THE INVENTION

Wavefront aberrations, diffraction limit and scatter are three optical defects in a human eye that degrade image quality and limit ocular performance. Wavefront aberrations can be determined with a Shack-Hartmann wavefront sensor. Diffraction limit can be calculated by using e.g. Raleigh's criteria. However, scatter, and its effects on visual performance, is difficult to accurately measure.

Many modern ophthalmic techniques require an accurate assessment of ocular performance to achieve effective results. For example, many techniques rely on the ability to accurately characterize the visual performance of an eye before and after a surgical procedure. By comparing the before and after results the effectiveness of the procedure can be determined.

It can be useful to measure the optical scattering of an eye before and after an ophthalmic procedure to determine the impact on the overall visual performance of an eye. In one specific example, it can be useful to determine the scattering of an eye that occurs after the implantation of an intraocular lens (IOL).

For these and other reasons there is a continuing need for improved devices and techniques to accurately determine and quantify ocular scattering.

BRIEF SUMMARY OF THE INVENTION

Embodiments of the present invention generally provide improved systems and methods for determining ocular scattering. These systems and methods can be used to quantify ocular scattering before and/or after a variety of different ophthalmic diagnostic procedures, and various surgical and non-surgical treatments. One embodiment provides a system and method for determining ocular scattering that uses two light detectors, with one detector configured to detect light over a relatively narrow angular range, and the other detector configured to detect light over a relatively large angular range. The data from the narrow angular range and the large angular range can then be analyzed to determine a measurement of ocular scattering.

In one embodiment a system to determine ocular scattering comprises a light source, a first detector, a second detector, and a processing system. The light source is configured to illuminate an eye such that light returns from the retina of the eye by scattering and/or reflection. The first detector is configured to detect a first portion of light returned from the eye and to generate first data indicative of the first portion of light. Specifically, the first detector is configured such that the first portion of light corresponds to light returned from the eye over a first angular range. The second detector is configured to detect a second portion of light returned from the eye and to generate second data indicative of the second portion of light. Specifically, the second detector is configured such that the second portion of light corresponds to light returned from the eye over a second angular range, where the second angular range is larger than the first angular range. The processing system is coupled to the first detector and the second detector and is configured to analyze (or fusion) the first data and the second data to determine a measurement of ocular scattering. Thus, the embodiment provides a device where returned light is detected over both a relatively narrow angular range and a relatively large angular range, and where data from both the narrow angular range and the large angular range is then analyzed to determine a measurement of ocular scattering.

The above summary and the following detailed description are merely exemplary, illustrative, and explanatory, and are not intended to limit, but to provide further explanation of the invention as claimed. Additional features and advantages of the invention will be set forth in the ensuing detailed descriptions that follow, and in part, will be apparent from the description, or may be learned by practicing various embodiments of the invention. The objectives and other advantages of the invention will be realized by the structures and methods particularly pointed out in the written description and claims as well as the accompanying drawings.

DETAILED DESCRIPTION OF THE INVENTION

Figure 1:
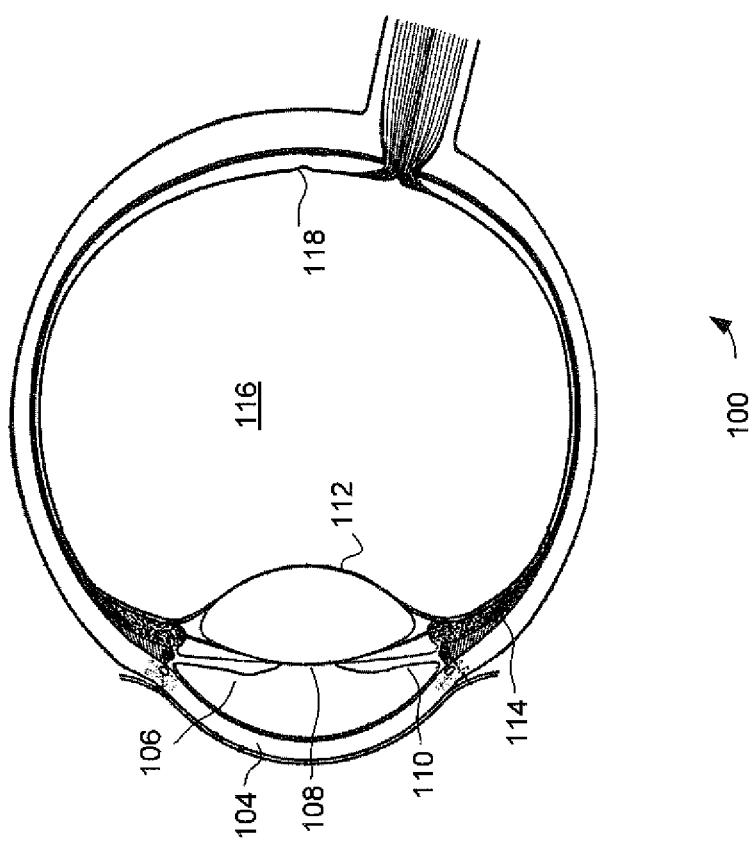
FIG. 1 is a cross-sectional side view of a human eye.

The figures and descriptions of the present invention have been simplified to illustrate elements that are relevant for a clear understanding of the present invention, while eliminating, for the purpose of clarity and brevity, many other elements found in typical ophthalmic techniques, systems, methods, lenses, and implantable optic apparatuses. Those of ordinary skill in the art may thus recognize that other elements and/or steps are desirable and/or required in implementing the present invention. However, because such elements and steps are well known in the art, and because they do not necessarily facilitate a better understanding of the present invention, those elements and steps are not discussed. This disclosure is directed to all applicable variations, changes, and modifications known to those skilled in the art. As such, the following detailed descriptions are merely illustrative and exemplary in nature and are not intended to limit the embodiments of the subject matter or the uses of such embodiments. As used in this application, the terms "exemplary" and "illustrative" mean "serving as an example, instance, or illustration." Any implementation described as exemplary or illustrative is not meant to be construed as preferred or advantageous over other implementations. Further, there is no intention to be bound by any expressed or implied theory presented in the preceding background of the invention, the brief summary, or the following detailed description.

The embodiments described herein provide systems and methods that can be used to quantify ocular scattering before and/or after a variety of different ophthalmic diagnostic procedures, and various surgical and non-surgical treatments. One embodiment provides a system and method for determining ocular scattering that uses two light detectors, with one detector configured to detect light over a relatively narrow angular range, and the other detector configured to detect light over a relatively large angular range. The data from the narrow angular range and the large angular range can then be analyzed to determine a measurement of ocular scattering.

In one embodiment a system to determine ocular scattering comprises a light source, a first detector; a second detector, and a processing system. The light source is configured to illuminate an eye such that light returns from the eye through optical interactions including scattering, reflection, diffraction, and/or refraction. The first detector is configured to detect a first portion of light returned from the eye and to generate first data indicative of the first portion of light. Specifically, the first detector is configured such that the first portion of light corresponds to light returned from the eye over a first angular range. The second detector is configured to detect a second portion of light returned from the eye and to generate second data indicative of the second portion of light. Specifically, the second detector is configured such that the second portion of light corresponds to light returned from the eye over a second angular range, where the second angular range is larger than the first angular range. The processing system is coupled to the first detector and the second detector and is configured to analyze the first data and the second data to determine a measurement of ocular scattering.

Thus, the embodiment provides a device where returned light is detected over both a relatively narrow angular range and a relatively large angular range, and where data from the narrow angular range and the large angular range are then be analyzed to determine a measurement of ocular scattering.

Turning to the drawings, FIG. 1 illustrates a simplified cross-sectional view of an exemplary human eye 100. In general, the eye 100 includes a cornea 104, an anterior chamber 106, a pupil 108, an iris 110, a lens 112, a ciliary muscle 114, a posterior chamber 116, and a retina 118. As briefly described earlier, many modern ophthalmic procedures require accurate measurements of the ocular system so that patients may be properly screened and treated. One type of ocular measurement is the determination of ocular scattering. In general, ocular scattering is the deflection of light rays in largely random directions caused by irregularities in ocular structure. Such irregularities can include variations in eye densities and/or composition fluctuations, voids, inclusions, and the presence of micro vacuoles inside the eye. These irregularities cause some portion of the light impacting the eye to scatter in largely random directions. Additionally, the presence of artificial ophthalmological devices such as IOLs can contribute to ocular scattering. In either case such scattering can result in a significant degradation of visual performance. In some specific examples a person suffering from ocular scattering may experience halo effects, light bursts and/or fuzziness in the perceived images. Finally, in some cases it may be desirable to measure the scattering of a cadaver eye or a model eye, in addition to measuring the scattering of a living eye such as eye 100.

Unfortunately, current techniques used to provide objective measurements of such scattering have had limited effectiveness. For example, some methods have relied upon topographers and aberrometers to quantify scattering. However, these techniques do not measure scattering directly, and thus only provide an indirect measurement of scattering. In contrast, the techniques described herein can provide an objective and direct measurement of ocular scattering using measurements from both a relatively wide angle detector and a relatively narrow angle detector.

Figure 2:
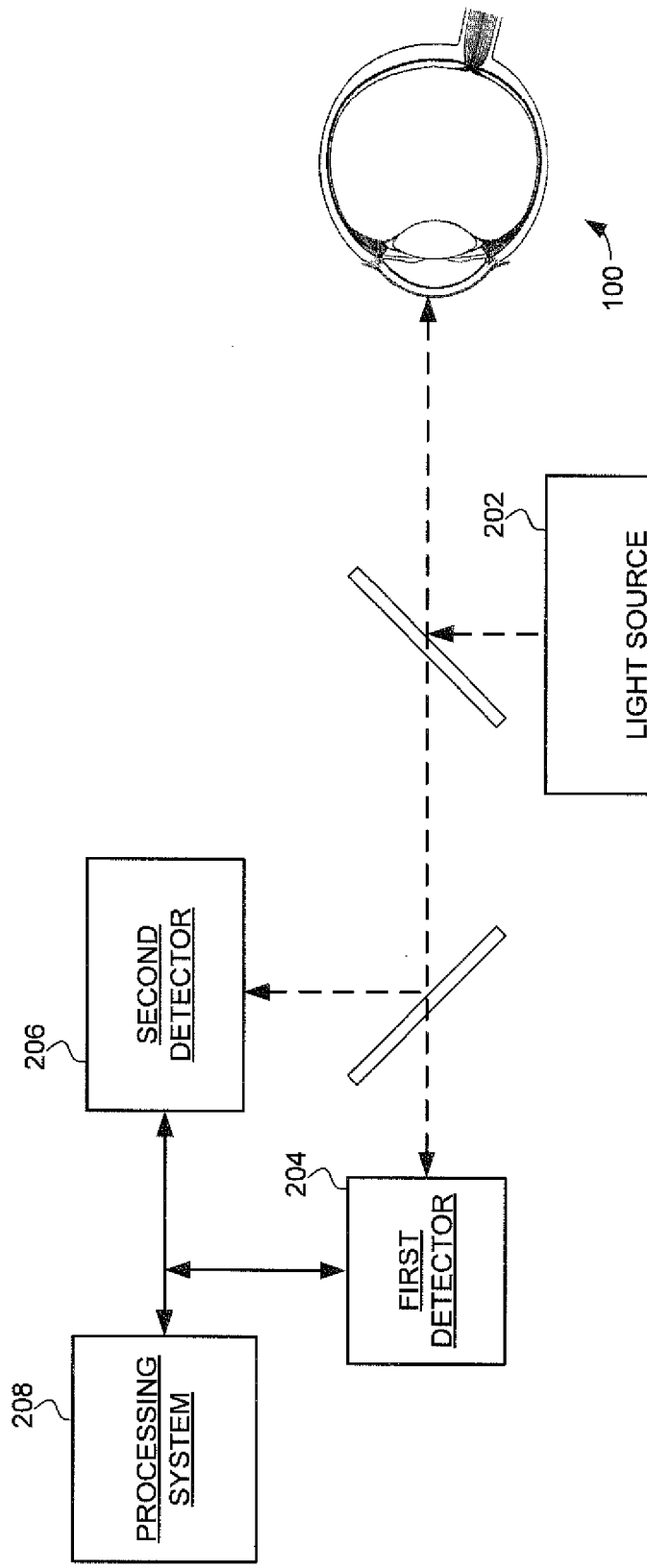
FIG. 2 is a schematic diagram of an ocular scattering system in accordance with an embodiment of the invention.

Turning now to FIG. 2, a simplified schematic view of an ocular scattering determination system 200 is illustrated. The system 200 includes a light source 202, a first detector 204, a second detector 206, and a processing system 208. In general, the light source 202 and associated optical elements are configured to illuminate the eye 100, resulting in some portion of the light deflecting from the eye and being received by the first detector 204 and the second detector 206.

In general, the first detector 204 is configured to detect a first portion of light deflected from the eye, where the first portion of light corresponds to light deflected over a first, relatively narrow, angular range. Similarly, the second detector 206 is configured to detect a second portion of light deflected from the eye, where the second portion of the light corresponds to light deflected over a second, relatively wide, angular range. In this context and in this application the term "deflected" can include light that is both reflected and scattered from the eye. Thus, the detectors 204 and 206 can be configured to detect light that is reflected and/or scattered from the eye.

The first detector 204 is further configured to generate first data indicative of the first portion of light, and the second detector 206 is further configured to generate second data indicative of the second portion of light. Thus, the first data corresponds to the light deflected from the eye over a relatively narrow angular range while the second data corresponds to the light deflected from the eye over a larger, relatively wide angular range.

The processing system 208 is coupled to the first detector 204 and the second detector 206 and is configured to receive the first data and the second data from the detectors. The processing system 208 is further configured to analyze the first data and the second data to determine a measurement of ocular scattering. As one example implementation, the processing system 208 is configured to analyze the first data and the second data to determine the measurement of the ocular scattering by integrating the first data over the first angular range and integrating the second data over the second angular range. In such an embodiment a comparison of the integration of the first data over the first angular range with the integration of the second data over the second angular range provides a measurement indicative of ocular scattering. Specifically, the integrations over the first and second angular ranges provide a stable measurement that can be used to objectively quantify the ocular scattering.

In another example implementation, the processing system 208 is configured to analyze the first data and the second data to determine the measurement of the ocular scattering by calculating a ratio between a difference in the first data and the second data and a summation of the first data and the second data. In this case, the ratio between the difference in the first data and the second data and the summation of the first data and the second data again provides a stable measurement that can be used to determine ocular scattering.

In another example, the processing system 208 is configured to analyze the first data and the second data to determine a measurement of the ocular scattering S by calculating:

$$S = 1 - \left[\frac{L_1 - L_2}{L_1 + L_2}\right] \quad \text{(Equation 1)}$$

where $L_1$ comprises an integration of the first data over the first angular range and where $L_2$ comprises an integration of the second data over the second angular range. In such an embodiment the calculation of S provides an objective measurement which is indicative of ocular scattering. Specifically, the integrations over the first and second angular ranges, and the use of a ratio of the difference and summation of such integrations provide an objective measurement of the ocular scattering.

As noted above, the first detector 204 is adapted to detect light over a relatively narrow angular range while the second detector 206 is adapted to detect light over a relative wide angular range. A variety of different ranges can be used. For example, in one embodiment the first angular range comprises less than +/−10 degrees and the second angular range comprises at least +/−60 degrees. In another embodiment the first angular range comprises less than +/−2 degrees, wherein the second angular range comprises at least +/−105 degrees (of angular range). In these examples the angular range is measured from the visual axis of the eye, although as reflected and/or passed by the optical elements of the system. Furthermore, in both these embodiments the difference between the relatively narrow and relatively wide angular range of the detectors facilitates the determination of ocular scattering.

In the embodiment shown in FIG. 2, the first detector 204 and the second detector 206 are each coupled to processing system 208 and configured to receive data from the detectors. In some embodiments the processing system 208 is additionally configured to the operation of the detectors 204 and 206. The processing system 208 can also be configured to control the light source 202. As described above, processing system 208 is also configured to analyze data from the detectors 204 and 206 to determine ocular scattering. To facilitate these and other actions the processing system 208 can comprise any suitable configuration of processing elements, including various computer memories, controllers, and other devices. For example, the processing system 208 can be implemented as software residing in memory and being executed by a processor, or as hardware hardcoded into a processing device, or any combination thereof.

A variety of different types of devices can be used to implement the first detector 204 and the second detector 206. As noted above, the first detector 204 is adapted to detect light over a relatively narrow angular range while the second detector 206 is adapted to detect light over a relative wide angular range. As will be described in greater detail below, in one embodiment the second detector 206 is configured to have a relatively wide sensing region such that it can receive light over the wide angular range. In another embodiment the second detector 206 is configured to move to receive light over the wide angular range. In some specific embodiments masked scanning techniques are used to facilitate narrow and wide angular range sensing.

As specific examples, the first detector 204 and/or second detector 206 can comprise charged-coupled devices (CCD), including both imaging CCDs and intensity CCDs. In other embodiments complementary metal-oxide-semiconductor (CMOS) detectors can be used. In yet other embodiments a wavefront sensor such as a Shack-Hartmann wavefront sensor could be used. Finally, in some embodiments spectral meters, photomulitplier tube (PMT) sensors, or small and large angle microscope sensors can be used.

A wide variety of different types of devices can be used to implement the light source 202. In general, the light source can comprise any suitable source of electromagnetic radiation. Usually a source in or near the visible band of the electromagnetic spectrum will be used. The light source 202 can be configured to generate light in the infrared, near infrared, or ultraviolet bands of the electromagnetic radiation. Furthermore, as used herein, the term "light" may be extended to mean electromagnetic radiation in or near the visible band of the electromagnetic spectrum, for example, in the infrared, near infrared, or ultraviolet bands of the electromagnetic radiation, or to mean electromagnetic radiation detectible by detectors (e.g. CCD) or that is otherwise useful in measuring the scattering. Additionally, the light source 202 can comprise single or multiple distinct sources of light. Furthermore the light source 202 can be monochromatic, polychromatic, polarized, or color-filtered. In some embodiments the light source 202 can be implemented to provide modulated intensity, with the modulated intensity providing the ability to mimic different light conditions. These mimicked conditions can include aberrations, light intensity variations or apodization, and spatial intensity variations.

In some embodiments the light source 202 can output light with a modulated wavefront phase. In one embodiment that will be described in greater detail below, the light source 202 is configured to move to facilitate determining ocular scattering over a wide range of angles.

Finally, in some variations, the light source 202 is an array of light sources or is otherwise configured to illuminate the eye with a pattern of light, such as a "checkerboard" pattern. As an example, a bundles of light forming a light pattern tha covers an area across the pupil may be used.

The system 200 can be implemented as a stand-alone device or as part of a larger diagnostic system or a larger ophthalmic laser system. For example, the system 200 can be implemented as part of an ophthalmic diagnostic and/or measurement system designed to provide one or more of wavefront aberrometry, topography, autorefractometry, pupillometry, optical coherence topography and aberrometry. More specifically, the system 200 may be incorporated into and implemented as part of the Abbott WaveScan WaveFron System, an ophthalmic diagnostic and measurement system that uses a Shack-Hartmann wavefront sensor to quantify aberrations throughout the entire optical system of the patient's eye, including second-order aberrations related to spherical error and cylindrical errors and higher order aberrations related to coma, trefoil, and spherical aberrations. An exemplary wavefront diagnostic system is described in U.S. Pat. No. 7,931,371, issued to Dai, which is incorporated by reference in its entirety. In this embodiment the scattering effects on image quality can be further defined by the phase structure from the aberrations and the measured intensity at the lenslet.

Alternatively, the system 200 may be incorporated into and implemented as part of a device or system that is used to generate pulsed laser beams, including non-ultraviolet (non-UV), ultrashort pulsed laser beams that have pulse durations that are measured in femtoseconds, as described in U.S. Pat. Nos. 4,764,930 and 5,993,438. Certain non-UV, ultrashort pulsed laser systems are used for ophthalmic surgeries. For example, U.S. Pat. No. 5,993,438 discloses a laser device for performing ophthalmic surgical procedures to effect high-accuracy corrections of optical aberrations. Further details of suitable systems for performing laser ophthalmic procedures can be found in commonly-assigned U.S. Pat. Nos. 4,665,913, 4,669,466, 4,732,148, 4,770,172, 4,773,414, 5,207,668, 5,108,388, 5,219,343, 5,646,791 and 5,163,934.

Figure 3:
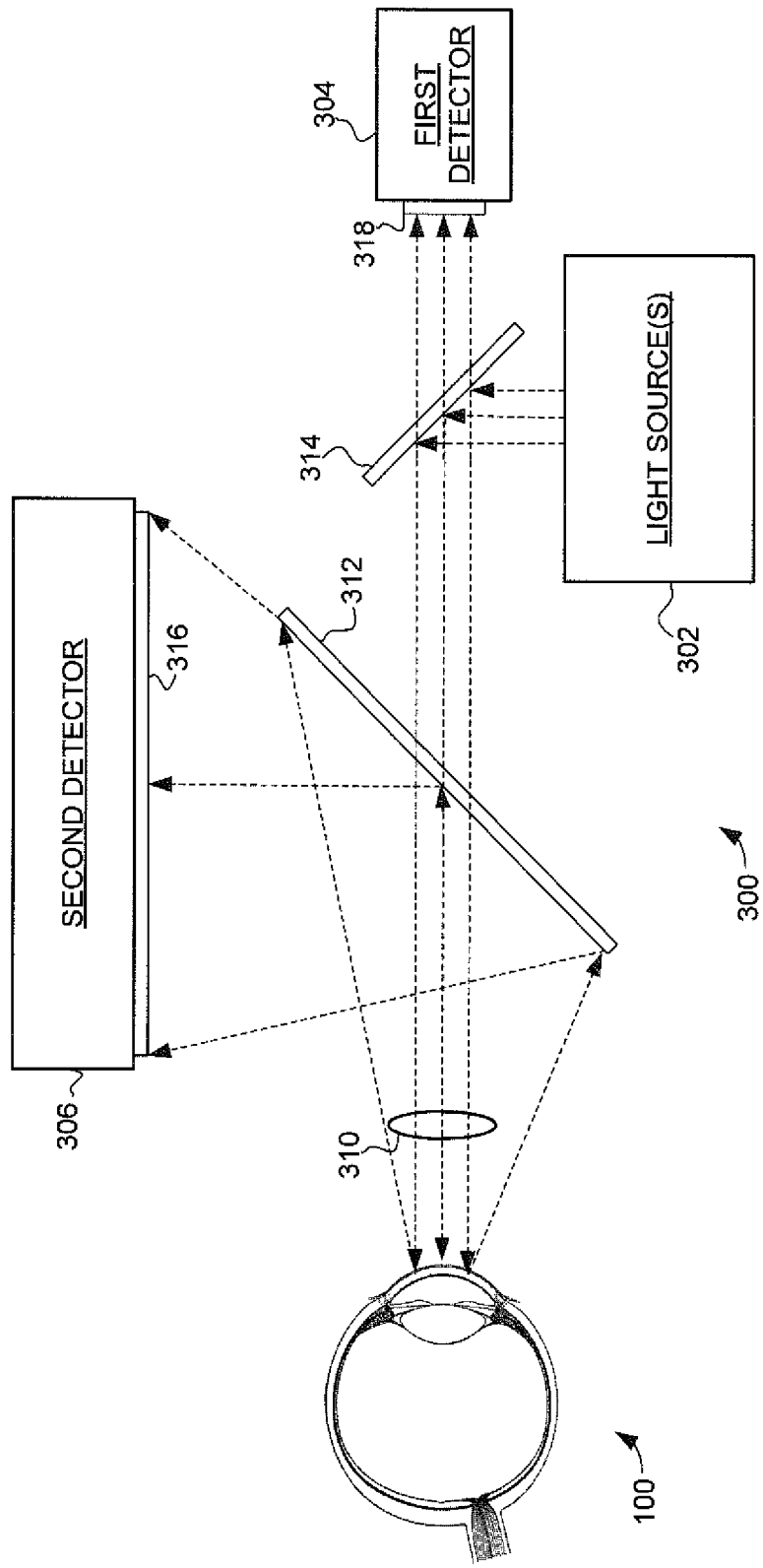
FIG. 3 is a schematic diagram of an ocular scattering system in accordance with an embodiment of the invention.

Turning now to FIG. 3, a schematic view of an ocular scattering determination system 300 is illustrated. The system 300 includes a light source 302, a first detector 304, a second detector 306, a lens 310, a beam splitter 312, and a beam splitter 314. In general, the light source 302 and associated optical elements are configured to illuminate the eye 100, resulting in some portion of the light deflecting from the eye 100. The lens 310 and beam splitter 312 result in a first portion of the deflected light being received by the first detector 304 and a second portion of the deflected light being received by the second detector 306. In this embodiment, the beam splitter 314 serves to reflect the light from the light source 302 to the eye 100. The lens 310 focuses the first portion of the light returning from the eye 100 on the sensing region 318 of the first detector 304. The beam splitter 312 directs the second portion of the light toward the sensing region 316 of the second detector 306. Specifically, the lens 310 and beam splitter 312 are configured such that the first portion of light corresponds to light deflected over a relatively narrow first angular range, while the second portion of light corresponds to light deflected over a relatively wide second angular range. In this illustrated embodiment, this configuration is further facilitated by the second detector 306 having a relatively large sensing region 316 compared to the sensing region 318 of the first detector.

The first detector 304 is further configured to generate first data indicative of the first portion of light, and the second detector 306 is further configured to generate second data indicative of the second portion of light. Thus, the first data corresponds to the light deflected from the eye over a relatively narrow angular range while the second data corresponds to the light deflected from the eye over a larger, relatively wide angular range. A processing system (not shown in FIG. 3) is coupled to the detectors and is configured to receive data from the detectors and analyze the data to determine a measurement of ocular scattering.

Figure 4:
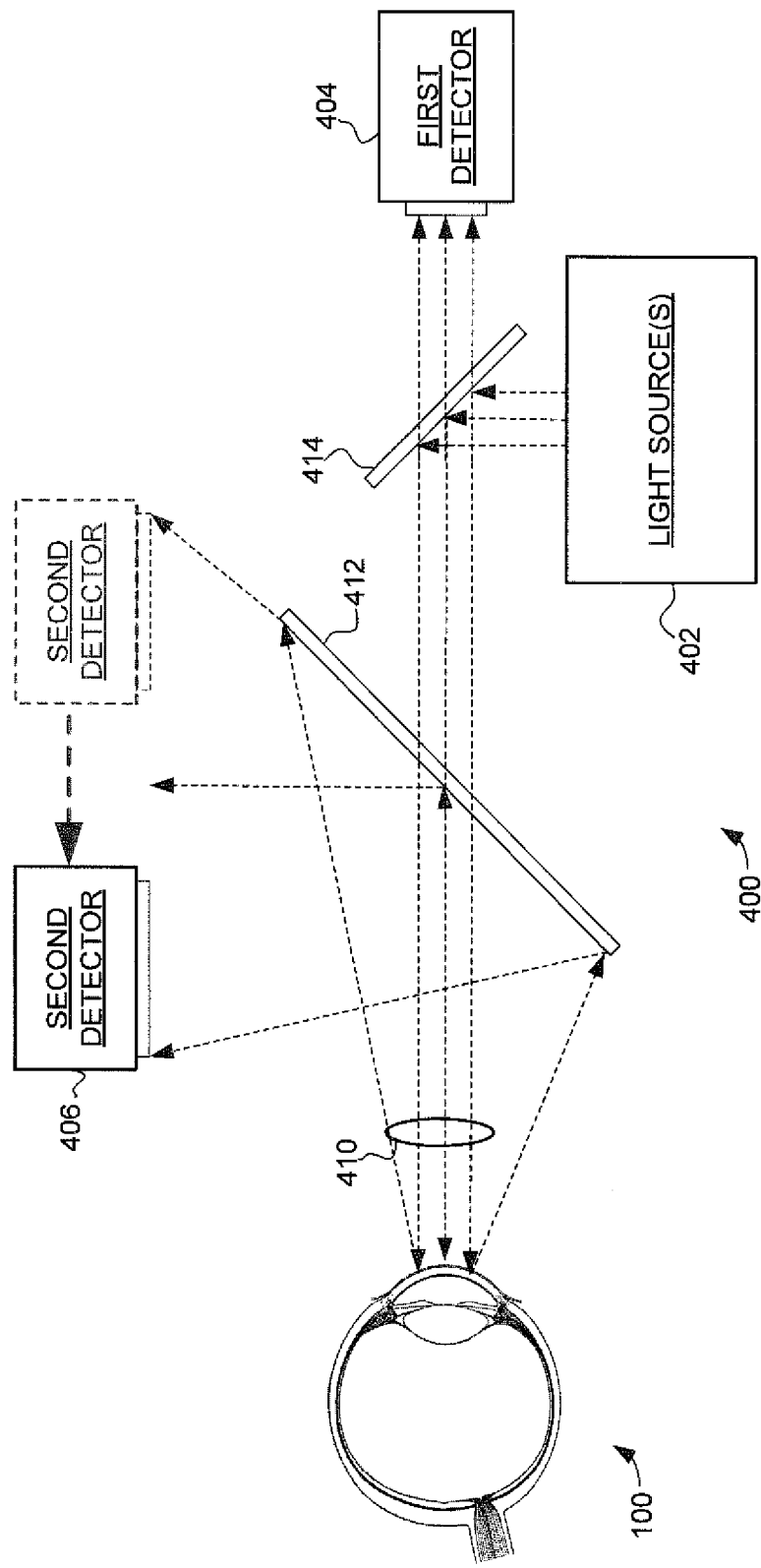
FIG. 4 is a schematic diagram of an ocular scattering system in accordance with an embodiment of the invention.

Turning now to FIG. 4, a schematic view of an ocular scattering determination system 400 is illustrated. In contrast with the embodiment illustrated in FIG. 3, this embodiment utilizes a moveable second detector. The system 400 again includes a light source 402, a first detector 404, a second detector 406, a lens 410, a beam splitter 412, and a beam splitter 414. Like the previous embodiment, the system 400 is configured such that a first portion of light that corresponds to light deflected over a relatively narrow first angular range is passed to the first detector 404, while a second portion of light that corresponds to light deflected over a relatively wide second angular range is passed to the second detector 406. However, in this embodiment the detection of the wide angular range of light is facilitated at least in part by the movement of the second detector 406. Such movement of the second detector 406 can be facilitated using any suitable structure and device. For example, a combination of control arms and motors can be used to controllably move the second detector 406. Thus, the second detector 406 can generate second data indicative of the light over the larger angular range.

Figure 5:
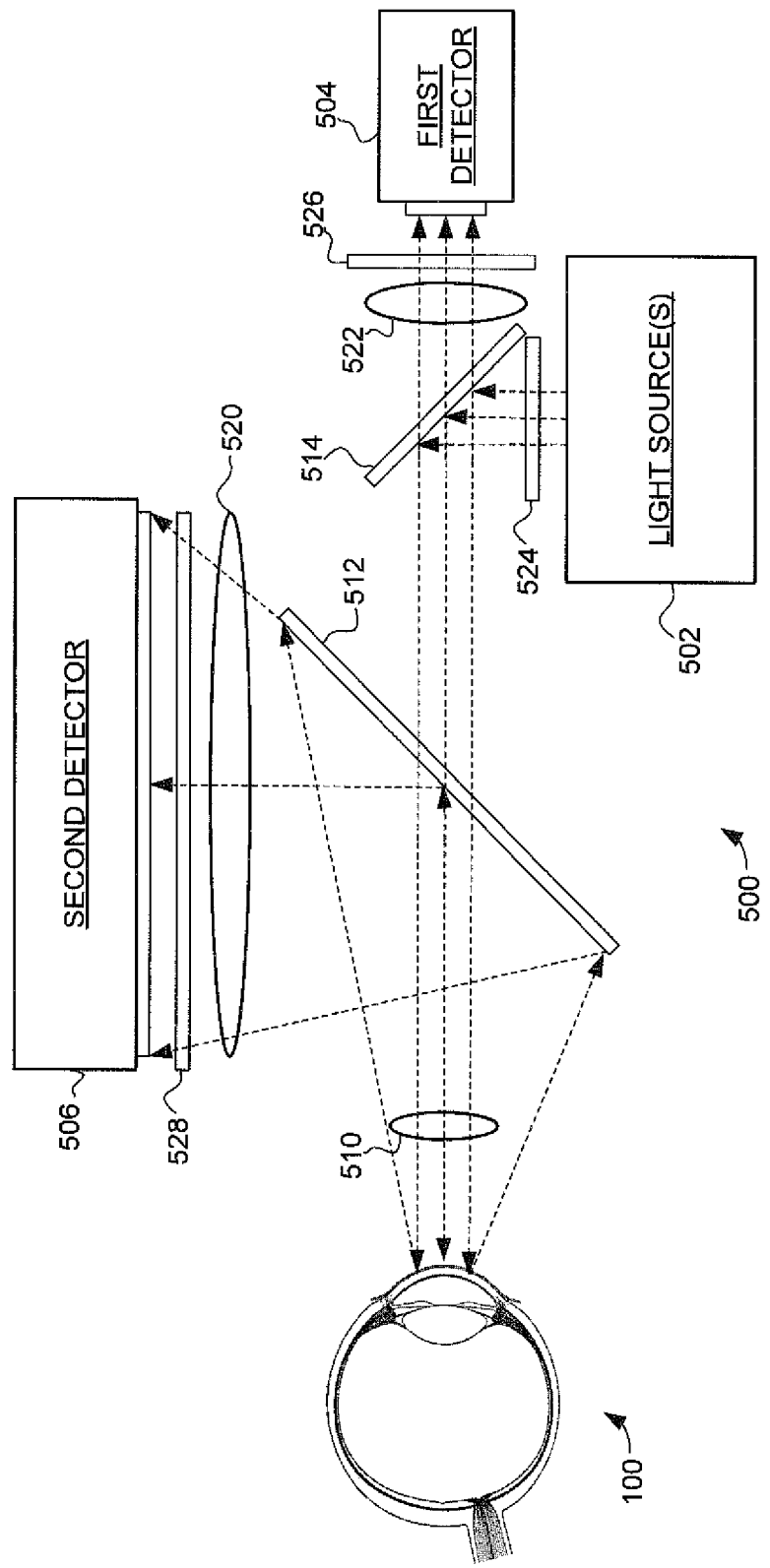
FIG. 5 is a schematic diagram of an ocular scattering system in accordance with an embodiment of the invention.

Turning now to FIG. 5, a simplified schematic view of an ocular scattering determination system 500 is illustrated. The system 500 again includes a light source 502, a first detector 504, a second detector 506, a lens 510, a beam splitter 512, and a beam splitter 514. Additionally, this embodiment includes lenses 520 and 522, and polarizers 524, 526 and 528.

As described above, the devices and techniques described above utilize the data from the first and second detectors to determine a measurement of the ocular scattering. In one example implementation the first and second data are integrated over the first angular range and second angular range respectively. In such an embodiment the integration of the first data over the first angular range and the integration of the second data over the second angular range provide a stable basis for measuring the ocular scattering.

Figure 6:
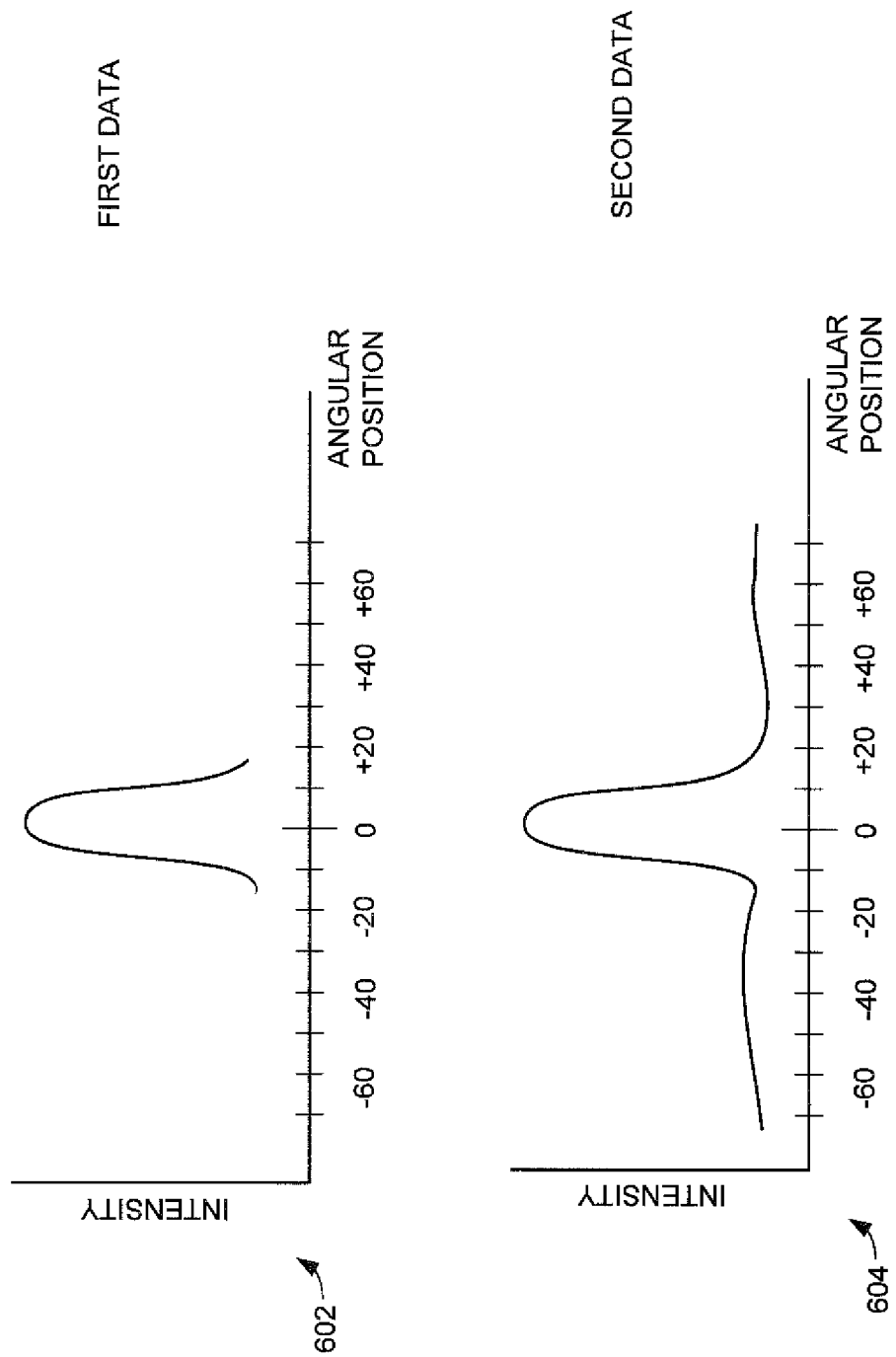
FIG. 6 are graphical representations of exemplary first data and second data in accordance with an embodiment of the invention.

Turning now to FIG. 6, graphical representations of exemplary first data and second data are illustrated in graphs 602 and 604. Specifically, graph 602 is a representation of exemplary first data generated from light deflecting over a relatively narrow first angular range and graph 604 is a representation of exemplary second data generated from light deflecting over a relatively wide second angular range. In this example the data corresponds to measured intensity at different angular positions relative to the eye. As can be seen in graph 602, the first data corresponds to an angular range of approximately +/−20 degrees. Likewise, the second data corresponds to an angular range of approximately +/−60 degrees. It should be noted that while graphs 602 and 604 illustrate the first data and the second data as each being profiles of data taken along one dimension of angular position, that this is just one example and that in other examples the first and second data could each comprise a "surface" of data taken along a two dimensional surface of angular position. Furthermore, it should be noted that in a typical embodiment the first data and second data comprise statistical light intensities that are angle dependent. In one specific example the first data comprises a first point spread intensity profile corresponding to the first angular range while the second data comprises a second point spread intensity profile corresponding to the second angular range. In other embodiments the first and second data can comprise multiple point spread intensity profiles with or without extended field of view.

Finally it should be noted that while graph 604 shows second data including data for scattering in the relatively narrow angular range, that this is just one example, and in other embodiments the second data may not include intensity data in the narrow range and only include data outside the narrow range. For example, the second data could include only data between −20 degrees and −60 degrees and between +20 degrees and +60 degrees. Such a result can be obtained by configuring the second detector to not detect in the "middle" range, or by using an appropriate pass-block filter to remove data for the middle range.

With the first data and second data as illustrated in FIG. 6, a measure of ocular scattering can be determined using those values. Specifically, the ocular scattering S can be determined by integrating the first data over the first angular range to determine $L_1$ and integrating the second data over the second angular range to determine $L_2$, and then calculating S using Equation 1 as described above. In such a technique because $L_1$ and $L_2$ are both integrated values they provide a stable basis for measuring the scattering, and thus the calculation of S provides a stable and objective measurement which is indicative of ocular scattering.

In this embodiment Equation 1 conceptually defines the scattering S as an intensity or energy loss caused by scattering. As another example, an intensity or energy can be defined as $L_1/L_0$ where $L_0$ is the initial input loss and the ratio is in logarithmic scale. Thus by measuring $L_0$, $L_1$ and $L_2$ simultaneously, the on-site scattering from the ocular system (including any IOL) and the effects of scattering on the image quality can be quantified and measured objectively. Furthermore, with the measured results the potential effects of the scattering on retinal image quality can then predicted.

Furthermore, in another embodiment the scattering dependence on angle can be determined from the first data and the second data. In such an embodiment the intensity at each angle can be determined and used to determine how scattering varies with angle. In another embodiment the scattering dependence on wavelength can be determined by measuring scattering at different wavelengths.

As described above, in one embodiment the ocular scattering system can be implemented as part of an ophthalmic aberrometry system that uses a Shack-Hartmann wavefront sensor to quantify aberrations. In this embodiment the first data can be collected using the Shack-Hartmann wavefront sensor and the second data collected using a suitable wide angle sensor. The use of the Shack-Hartmann wavefront sensor further allows for the determination of the phase structure from the aberrations and the measured intensity at the lenslet. Furthermore, such a system can be synchronized by angle (by varying angle) and by chromate (by varying wavelength) sampling mechanisms through scanning. In this embodiment the signal integration can be based on single-explosion signals or longtime explosions for Again, this paragraph describes some examples from the disclosure that we did not really discuss.

The embodiments described herein thus provide techniques for accurate determination of ocular scattering. Such techniques can be used for any diagnostic procedure where such a determination is required. Furthermore, these techniques can thus be used to improve the effectiveness of a wide variety of different ophthalmic procedures.

This disclosure has been provided in an exemplary form with a certain degree of particularity, and describes the best mode contemplated of carrying out the invention to enable a person skilled in the art to make or use embodiments of the invention. Those skilled in the art will understand, however, that various modifications, alternative constructions, changes, and variations can be made in the system, method, and parts and steps thereof, without departing from the spirit or scope of the invention. Hence, the disclosure is not intended to be limited to the specific examples and designs that are described. Rather, it should be accorded the broadest scope consistent with the spirit, principles, and novel features disclosed as generally expressed by the following claims and their equivalents.

What is claimed is:

1. A system for determining ocular scattering, the system comprising:
    a light source configured to illuminate an eye;
    a first detector configured to detect a first portion of light deflected from the eye and to generate first data indicative of the first portion of light, wherein the first detector is configured such that the first portion of light corresponds to light deflected from the eye over a first angular range;
    a second detector configured to detect a second portion of light deflected from the eye and to generate second data indicative of the second portion of light, wherein the second detector is configured such that the second portion of light corresponds to light deflected from the eye over a second angular range, wherein the second angular range is larger than the first angular range;
    a processing system coupled to the first detector and the second detector, the processing system configured to analyze the first data and the second data to determine a measurement of ocular scattering.

2. The system of claim 1 wherein the processing system is configured to analyze the first data and the second data to determine the measurement of the ocular scattering by integrating the first data over the first angular range and integrating the second data over the second angular range.

3. The system of claim 1 wherein the processing system is configured to analyze the first data and the second data to determine the measurement of the ocular scattering by calculating a ratio between a difference in the first data and the second data and a summation of the first data and the second data.

4. The system of claim 1 wherein the first data comprises a first point spread intensity profile corresponding to the first angular range and wherein the second data comprises a second point spread intensity profile corresponding to the second angular range.

5. The system of claim 1 wherein the processing system is configured to analyze the first data and the second data to determine the measurement of the ocular scattering by calculating:

$$1 - \left[\frac{L_1 - L_2}{L_1 + L_2}\right]$$

where $L_1$ comprises an integration of the first data over the first angular range and where $L_2$ comprises an integration of the second data over the second angular range.

6. The system of claim 1 wherein the first detector and the second detector comprise detectors selected from the group consisting of a light phase sensor and an intensity sensor.

7. The system of claim 1 wherein the first detector comprises a sensor selected from the group consisting of: Shack-Hartmann wavefront sensor, charge-coupled device sensor, complementary metal-oxide-semiconductor sensor, photomulitplier tube sensor, small angle microscope sensor, and spectral meter.

8. The system of claim 1 wherein the second detector comprises a sensor selected from the group consisting of: charge-coupled device sensor, complementary metal-oxide-semiconductor sensor, photomulitplier tube sensor, large angle microscope sensor, and spectral meter.

9. The system of claim 1 wherein the second detector is configured to move to detect the second portion of light over the second angular range.

10. The system of claim 1 wherein the light source is configured to move to generate scattered light over the second angular range.

11. The system of claim 1 wherein the light source is configured to generate light having a modulated wavefront phase.

12. The system of claim 1 wherein the light source is configured to generate light having a modulated intensity to mimic different light conditions.

13. The system of claim 1 wherein the first angular range comprises less than +/−10 degrees and wherein the second angular range comprises at least +/−60 degrees.

14. The system of claim 1 wherein the first angular range comprises less than +/−2 degrees and wherein the second angular range comprises at least +/−110 degrees.

15. The system of claim 1 wherein the eye is selected from a group consisting of a living eye, a cadaver eye, or a model eye.

16. The system of claim 1 wherein a function of the eye is modified with an ophthalmological device.

17. A system for determining ocular scattering, the system comprising:
    a light source configured to illuminate an eye;
    a first detector configured to detect a first portion of light deflected from the eye and to generate first data indicative of the first portion of light, and where the first detector is configured such that the first portion of light corresponds to light deflected from the eye over a first angular range;
    a second detector configured to detect a second portion of light deflected from the eye and to generate second data indicative of the second portion of light, and where the second detector is configured such that second portion of light corresponds to light deflected from the eye over a second angular range, where the second angular range is larger than the first angular range;

a processing system coupled to the first detector and the second detector, the processing system configured to:
receive the first data and the second data;
integrate the first data over the first angular range to determine a value $L_1$,
integrate the second data over the second angular range to determine a value $L_2$,
determine a measurement of ocular scattering by calculating;

$$1 - \left[\frac{L_1 - L_2}{L_1 + L_2}\right]$$

and outputting the measurement of ocular scattering.

18. A method for determining ocular scattering, the method comprising:
illuminating an eye;
detecting a first portion of light deflected from the eye and generating first data indicative of the first portion of light, where the first portion of light corresponds to light deflected from the eye over a first angular range;
detecting a second portion of light deflected from the eye and generating second data indicative of the second portion of light, where the second portion of light corresponds to light deflected from the eye over a second angular range, and where the second angular range is larger than the first angular range; and
analyzing the first data and the second data to determine a measurement of ocular scattering.

19. The method of claim 18 wherein the analyzing the first data and the second data to determine the measurement of the ocular scattering comprises integrating the first data over the first angular range and integrating the second data over the second angular range.

20. The method of claim 18 wherein the analyzing the first data and the second data to determine the measurement of the ocular scattering comprises calculating a ratio between a difference in the first data and the second data and a summation of the first data and the second data.

21. The method of claim 18 wherein the first data comprises a first point spread intensity profile corresponding to the first angular range and wherein the second data comprises a second point spread intensity profile corresponding to the second angular range.

22. The method of claim 18 wherein the analyzing the first data and the second data to determine the measurement of the ocular scattering comprises calculating:

$$1 - \left[\frac{L_1 - L_2}{L_1 + L_2}\right]$$

where $L_1$ comprises an integration of the first data over the first angular range and where $L_2$ comprises an integration of the second data over the second angular range.

23. The method of claim 18 wherein the detecting the first portion of light deflected from the eye and wherein detecting the second portion of light deflected from the eye comprises detecting light intensity.

24. The method of claim 18 wherein the detecting the first portion of light deflected from the eye and wherein detecting the second portion of light deflected from the eye comprises detecting light phase.

25. The method of claim 18 wherein the detecting the second portion of light deflected from the eye comprises moving a detector.

26. The method of claim 18 wherein the detecting the second portion of light deflected from the eye comprises moving a light source.

27. The method of claim 18 wherein the illuminating the eye comprises illuminating with light having a modulated wavefront phase.

28. The method of claim 18 wherein the illuminating the eye comprises illuminating with light having a modulated intensity to mimic different light conditions.

29. The method of claim 18 wherein the first angular range comprises less than +/−10 degrees and wherein the second angular range comprises at least +/−60 degrees.

30. The method of claim 18 wherein the first angular range comprises less than +/−2 degrees and wherein the second angular range comprises at least +/−110 degrees.

31. The method of claim 18 wherein the eye is selected from a group consisting of a living eye, a cadaver eye, or a model eye.

32. The method of claim 18 wherein a function of the eye is modified with ophthalmological device.

* * * * *